Figure 1:
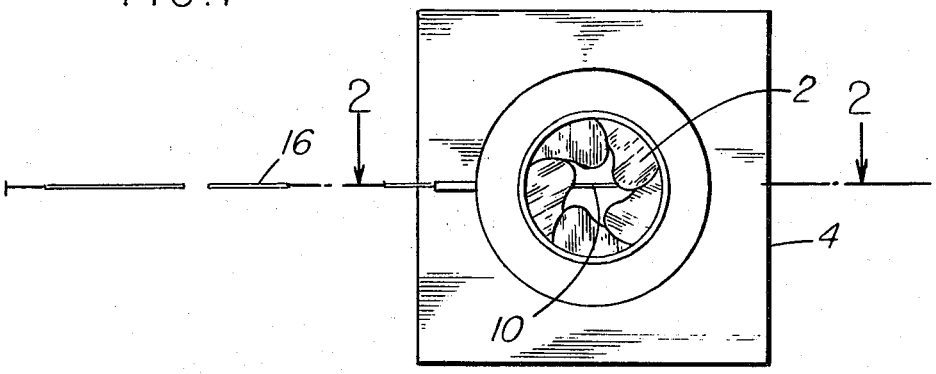
Figure 2:
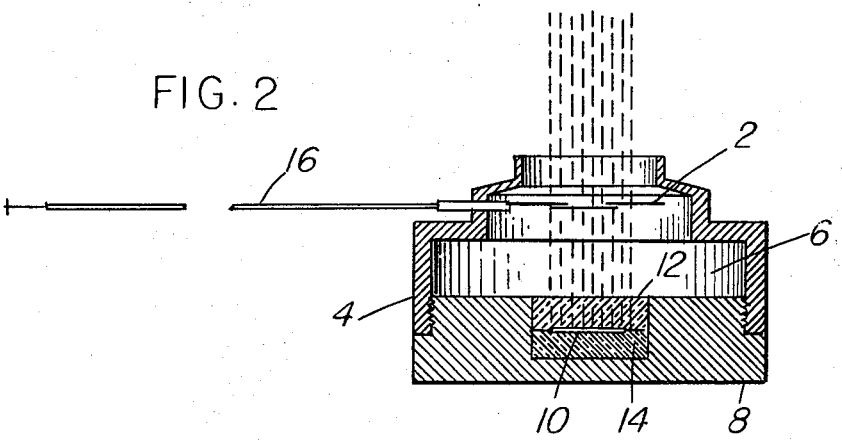
Figure 3:
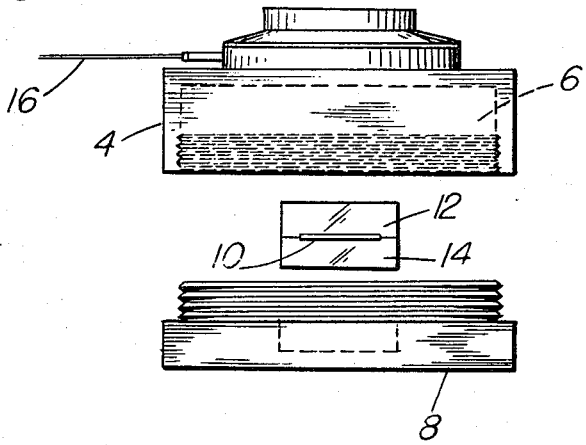

DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JUNE 1, 1976

947 O.G. 12

T947,004

APPARATUS FOR SEMI-QUANTITATIVE MEASUREMENT OF CHEMICAL RESPONSE TO U.V. RADIATION

George L. Collins, 44 The Fellsway, Murray Hill, N.J. 07974, and William V. Garruto, 331 W. Scott Ave., Rahway, N.J. 07065

Filed Jan. 30, 1975, Ser. No. 545,271
Int. Cl. G01n *21/06. 33/44*
U.S. Cl. 23—230 R
1 Sheet Drawing. 7 Pages Specification

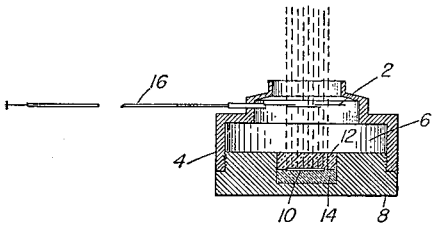

A device for semi-quantitative measurement of chemical response of photoinitiators and resin systems to U.V. radiation which comprises a shutter positioned on a housing having a cavity within. The housing is separable into an upper and lower portion giving access to the cavity. A U.V. curable resin is placed within the aluminum housing and the entire assembly is passed under a U.V. lamp where the shutter is activated. The rate and/or extent of reaction can be determined by analysis of the exposed sample APPARATUS FOR SEMI -QUANTITATIVE MEASUREMENT OF CHEMICAL RESPONSE TO U. V. RADIATION Original Filed Jan. 30, 1975